United States Patent [19]

Weaver et al.

[11] 4,012,372
[45] Mar. 15, 1977

[54] PHTHALIMIDYL-AZO-TETRAHYDRO-QUINOLINE COMPOUNDS

[75] Inventors: Max Allen Weaver; Jean Carroll Fleischer, both of Kingsport, Tenn.

[73] Assignee: Eastman Kodak Company, Rochester, N.Y.

[22] Filed: Apr. 2, 1975

[21] Appl. No.: 564,527

Related U.S. Application Data

[63] Continuation of Ser. No. 376,047, July 2, 1973, abandoned.

[52] U.S. Cl. .................. 260/155; 260/154; 260/243 R; 260/247.2 A; 260/247.5 GP; 260/256.5 R; 260/283 CN; 260/283 S; 260/287 T; 260/302 S; 260/302 SD; 260/306; 260/307 G; 260/308 R; 260/326 S; 260/326 N
[51] Int. Cl.² .......................................... C09B 29/36
[58] Field of Search ........................... 260/154, 155

[56] References Cited

FOREIGN PATENTS OR APPLICATIONS 1,544,370   7/1969   Germany ................... 260/155

*Primary Examiner*—Charles F. Warren
*Attorney, Agent, or Firm*—Donald W. Spurrell; Daniel B. Reece, III

[57] ABSTRACT

Monoazo compounds containing a phthalimidyl diazo component the aromatic ring of which can be substituted with one or two substituents, and the nitrogen of which may be substituted, and a 1,2,3,4-tetrahydroquinoline disperse azo dye coupling component which contains at least one alkyl substituent, are useful for dyeing cellulose acetate, nylon, and especially polyester fibers on which the compounds exhibit good fastness and dyeability properties.

8 Claims, No Drawings

PHTHALIMIDYL-AZO-TETRAHYDROQUINOLINE COMPOUNDS

This is a continuation of Application Ser. No. 376,047, filed July 2, 1973, now abandoned.

This invention relates to certain novel azo compounds and, more particularly, to phthalimidyl-azo-tetrahydroquinoline compounds and to polyester fibers dyed therewith.

The compounds of our invention have the general formula

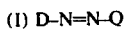

(I) D–N=N–Q wherein
D is a phthalimidyl group having the formula

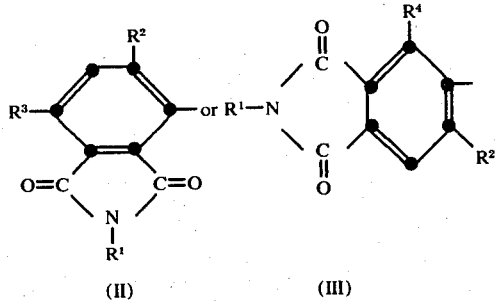

wherein $R^1$ is hydrogen or an organic radical having a molecular weight of not more than 200;

$R^2$ is hydrogen, lower alkyl, halogen, cyano, nitro, lower alkylsulfonyl, arylsulfonyl, arylthio, aryl-lower-alkylthio, cyclohexylthio, lower alkoxy, aryloxy, 2-benzothiazolylthio, 2-thiazolylthio, 2-thiadiazolythio, 2-oxadiazolythio, 1,2,4-triazol-3-ylthio, or 2-pyrimidinylthio;

$R^3$ is hydrogen, halogen or nitro; and $R^4$ is hydrogen, lower alkyl, halogen, cyano, nitro, lower alkylsulfonyl, arylsulfonyl, arylthio, aryl-lower-alkylthio, cyclohexylthio, lower alkoxy, aryloxy, 2-benzothiazolylthio, 2-thiazolylthio, 2-thiadiazolylthio, 2-oxadiazolylthio, 1,2,4-triazol-3-ylthio or 2-pyrimidinylthio; and Q is a 1,2,3,4-tetrahydroquinoline disperse azo dye coupling component.

The novel compounds of the invention produce orange to blue shades on polyester, polyamide and cellulose acetate fibers when applied thereto according to conventional disperse dyeing procedures. The compounds, in general, exhibit good to excellent dyeability properties, fastness to light and resistance to sublimation.

The substituents encompassed by the generic terminology appearing in the definitions of $R^1$, $R^2$, $R^3$ and $R^4$ are well known in the art. As used herein to describe a group containing an alkyl moiety, lower designates a carbon content of up to about four carbon atoms. The aryl moiety of the aryl and aryl-containing groups such as aroyl and arylene can be unsubstituted phenyl and phenyl substituted with nonionic substituents, such as lower alkyl, lower alkoxy, halogen, cyano, lower alkoxycarbonyl, etc.

Our novel azo compounds are prepared by diazotizing a halogenated or nitrated aminophthalimide, including halo and nitro derivatives thereof, and coupling the resulting diazonium salt with a 1,2,3,4-tetrahydroquinoline compound having the formula H-Q. If desired, any halogen atom present on the diazo component of the resulting azo compound in a position ortho to the azo group can be replaced with various groups by the reaction thereof with nucleophiles such as cyanides, sulfinates, mercaptides, alkoxides, aryloxides, etc.

The 3-aminophthalimides in which $R^1$ is hydrogen are prepared by reacting 3-nitrophthalic anhydride with ammonia followed by the reduction of the nitro groups to the amino group whereas the analogous 4-amino compounds are prepared by reacting phthalic anhydride with ammonia followed by nitration and reduction. The corresponding aminophthalimide compounds in which $R^1$ is a substituent are prepared by the mentioned techniques except that a primary amine is substituted for the ammonia. Alternatively, the aminophthalimide compounds in which $R^1$ is a substituent can be prepared by reacting either phthalimide or a nitrophthalimide with an alkylating agent such as an aliphatic halide. The particular substitutent represented by $R^1$ is, in general, not critical. However, since our novel azo compounds are disperse dye compounds, substituent $R^1$ is free of water-solubilizing groups such as sulfonate and carboxylate salt groups. The primary amines from which substitutent $R^1$ can be derived have the formula $R^1$-$NH_2$ in which $R^1$ is an unsubstituted or substituted aliphatic, alicyclic, aromatic or heterocyclic residue having a molecular weight of not more than 200. In view of the vast number of primary amines and aliphatic halides which are known and/or can be synthesized by conventional procedures and since the substituent represented by $R^1$ is not critical, no further elaboration on the groups represented by $R^1$ is warranted. However, it is preferred that substituent $R^1$ be devoid of amino groups, including unsubstituted and substituted amino groups, since such groups can affect detrimentally the synthesis of the azo compounds. The substituents described above in the definition of $R^2$ and those described hereinafter are typical of the groups which $R^1$ can represent.

Both the 3-aminophthalimides and 4-aminophthalimides can be halogenated to give the corresponding dihalo compounds, 3-amino-4,6-dihalophthalimides and 4-amino-3,5-dihalophthalimides. If only one equivalent of halogen is employed, the 4-aminophthalimides can be monohalogenated in the 5-position. The 3-amino-6-nitrophthalimides are prepared by nitrating the corresponding 3-acetamidophthalimides followed by hydrolysis of the acetamido group to the free amine. The 3-amino-6-nitrophthalimides can be halogenated to yield the 3-amino-4-halo-6-nitrophthalimides. The nitration and halogenation reactions used to synthesize the diazo precursors are conducted according to conventional techniques. Preferably, bromine is used as the halogenating agent.

The aminophthalimides prepared as described in the preceding paragraph are diazotized and coupled with a 1,2,3,4-tetrahydroquinoline coupler to yield azo compounds having the formulas

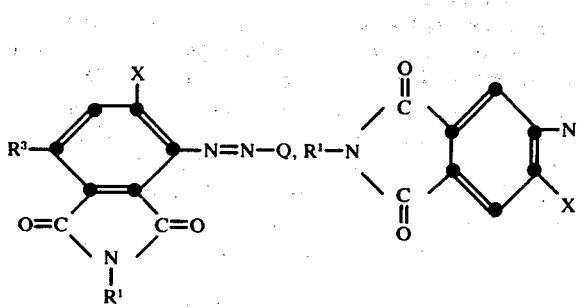 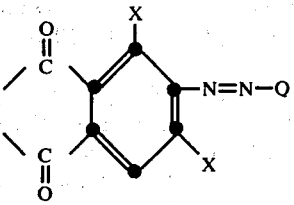

wherein R¹, R³ and Q are defined above and X is hydrogen or halogen, preferably bromine. As mentioned above, the halogen atom X can be replaced by reacting the azo compounds with various nucleophiles.

The groups represented by Q are well known in the art and are characterized by being free of groups, such as sulfonates, which will render the compounds of formula (I) water-soluble. Some of the patent literature describing disperse azo dye coupling components is set forth in application Ser. No. 71,365 filed Sept. 11, 1970, now U.S. Pat. No. 3,829,410, issued Aug. 13, 1974. Typical of the substituents represented by Q are the groups represented by the formula

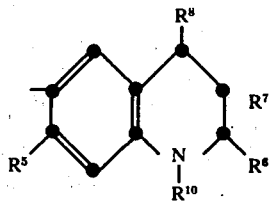

wherein
$R^5$ is hydrogen, lower alkyl, lower alkoxy, halogen or a group having the formula -NH-$R^9$ in which $R^9$ is an organic acyl group;
$R^6$ is lower alkyl or, when $R^7$ and $R^8$ each is methyl, $R^6$ is methyl;
$R^7$ and $R^8$ each is hydrogen or methyl;
$R^{10}$ is alkyl containing one to about eight carbon atoms; cyclohexyl; cyclohexyl substituted with lower alkyl; or lower alkyl substituted with hydroxy, lower alkoxy, aryl, aryloxy, cyclohexyl, cyano, lower alkanoyloxy, lower alkoxycarbonyl, lower alkoxycarbonyloxy, aroyloxy, lower alkylcarbamoyloxy, arylcarbamoyloxy, or a group having the formula

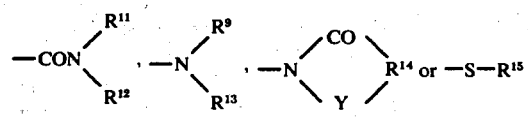

wherein
$R^{11}$ individually is hydrogen, lower alkyl or aryl;
$R^{12}$ individually is hydrogen or lower alkyl;
$R^{11}$ and $R^{12}$ collectively are -(CH₂)₅- or -CH₂CH₂OCH₂CH₂-;
$R^9$ is an organic acyl radical;
$R^{13}$ is hydrogen, lower alkyl, aryl, or cyclohexyl;
$R^{14}$ is ethylene, propylene, trimethylene, o-cyclohexylene, or o-arylene, or when Y is —CO—, $R^{13}$ also can be —NHCH₂—, —N(lower alkyl)CH₂—, —SCH₂—, —OCH₂—, or —CH₂OCH₂—;
Y is —CH₂—, —CO—, or —SO₂—; and
$R^{15}$ is aryl, benzyl, cyclohexyl, 1,2,4-triazol-3-yl, or 2-benzothiazolyl.

The organic acyl radicals represented by $R^9$ preferably are formyl, lower alkanoyl, aroyl, cyclohexylcarbonyl, lower alkoxycarbonyl, aryloxycarbonyl, lower alkylsulfonyl, cyclohexylsulfonyl, arylsulfonyl, carbamoyl, lower alkylcarbamoyl, arylcarbamoyl, furoyl, etc. The alkanoyl groups can be substituted with substituents such as halogen, aryl, cyano, lower alkoxy, aryloxy, benzyloxy, lower alkylthio, lower alkylsulfonyl, lower alkanoyloxy, etc. The alkylsulfonyl groups also can be substituted, for example, with cyano, hydroxy, halogen and the like. The alkoxycarbonyl groups can be substituted, for example, with hydroxy, alkoxy and cyano. Acetyl, propionyl, butyryl, cyanoacetyl, chloroacetyl, trifluoroacetyl, phenylacetyl, methoxyacetyl, methylthioacetyl, methylsulfonylacetyl, methoxycarbonyl, propoxycarbonyl, butoxycarbonyl, methylsulfonyl, ethylsulfonyl, propylsulfonyl, butylsulfonyl, 2-cyanoethylsulfonyl, 2-hydroxyethylsulfonyl, and 2-chloroethylsulfonyl are examples of the alkanoyl, alkoxycarbonyl and alkylsulfonyl groups which $R^9$ can represent. Dimethylcarbamoyl, ethylcarbamoyl, propylcarbamoyl, butylcarbamoyl, phenylcarbamoyl and dimethylcarbamoyl are examples of the substituted carbamoyl groups. The unsubstituted and substituted alkanoyl, aroyl and alkoxycarbonyl groups are preferred.

The substituted alkyl groups represented by $R^{10}$ preferably are arylmethyl, arylethyl, cyclohexylmethyl, 2-cyanoethyl, or a group having the formula —Z—$R^{16}$ in which Z is ethylene, propylene, trimethylene, or tetramethylene and $R^{16}$ is any of the substituents, except aryl, cyano, and cyclohexyl, which can be present on the substituted alkyl groups represented by $R^{10}$ as defined above.

A group of our novel compounds which are especially preferred because of their cost:performance ratio are those having the formula

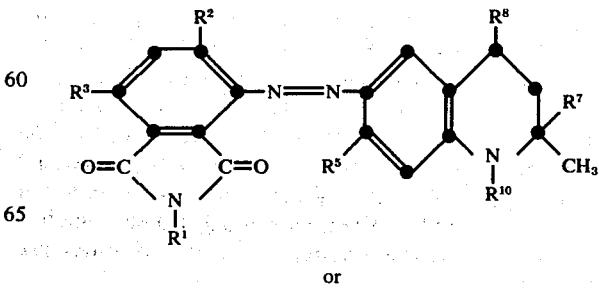

or

-continued

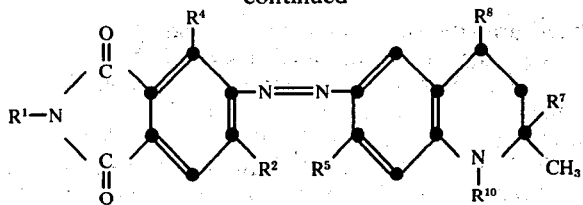

wherein
$R^1$ is lower alkyl; arylmethyl; cyclohexylmethyl; 2-cyanoethyl; 2-carbamoylethyl; aryl; cyclohexyl; or the group —Z—$R^{17}$ in which Z is ethylene, propylene, or trimethylene and $R^{17}$ is succinimido, glutarimido, phthalimido, hydroxy, lower alkanoyloxy, 2-pyrrolidinone, or lower alkoxy;
$R^2$ is hydrogen, chlorine, bromine or cyano;
$R^3$ is hydrogen, chlorine, bromine or nitro;
$R^4$ is hydrogen, chlorine, bromine or cyano;
$R^5$ is hydrogen, methyl, lower alkanoyl, benzamido or lower alkoxycarbonyl;
$R^7$ and $R^8$ each is hydrogen or methyl; and
$R^{10}$ is lower alkyl; allyl; cyclohexyl; arylmethyl; cyclohexylmethyl; 2-cyanoethyl; 2-carbamoylethyl; N-lower-alkyl-2-carbamoylethyl; N,N-di-lower-alkyl-2-carbamoylethyl; or the group —Z—$R^{16}$ in which Z is ethylene, propylene or trimethylene and $R^{16}$ is hydroxy, lower alkanoyloxy, lower alkoxycarbonyl, lower alkoxycarbonyloxy, succinimido, glutarimido, phthalimido, 2-pyrrolidinono, lower alkanoylamido, lower alkoxy or the group

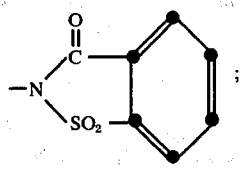

in which each aryl moiety is phenyl, tolyl, anisyl, ethoxyphenyl or chlorophenyl.

Our novel compounds and their synthesis and use are further illustrated by the following examples.

EXAMPLE 1

To 2-aminoethanol (12.2 g.) is added portionwise at 100°–125° C. 4-nitrophthalic anhydride (38.6 g.) with manual stirring. The mixture is heated gradually to 150° C. and kept at 150°–160° C. for 1 hr. with occasional stirring. The reaction mixture is cooled slightly and 50 ml. of ethanol is added. This solution is then drowned into 200 ml. of water. The product, N-(2-hydroxyethyl)-4-nitrophthalimide, is collected by filtration, washed with water and dried in air. It melts at 118°–119° C. and weighs 30.0 g.

EXAMPLE 2

N-(2-Hydroxyethyl)-4-nitrophthalimide (30.0 g.), ethanol (300 ml.), and Raney nickel (3.0 g.) are mixed and hydrogenated at 100° C. and 1500 psi. until hydrogen uptake ceases. The hot solution is filtered to remove the Raney nickel and the solvent evaporated to yield 4-amino-N-(2-hydroxyethyl)-phthalimide, the amine which melts at 171°–173° C.

EXAMPLE 3

A mixture of 4-nitrophthalimide (38.4 g.), iodoethane (46.8 g.), potassium carbonate (27.6 g.), and N,N-dimethylformamide (200 ml.) are heated and stirred at 95°–100° C. for 2 hr. An additional amount of iodoethane (46.8 g.) is added and the reaction mixture heated 4 hr. longer at 95°–100° C. The reaction mixture is drowned into 1500 ml. of water. The product, N-ethyl-4-nitrophthalimide, is collected by filtration, washed with water and recrystallized from methanol. It melts at 113°–114° C.

EXAMPLE 4

N-Ethyl-4-nitrophthalimide (28.0 g.) is hydrogenated in 400 ml. of ethanol and in the presence of Raney nickel catalyst (10 g.) at 100° C. and 1500 psi. pressure. The reaction mixture is filtered to remove the catalyst and the filtrate is concentrated to yield the product, 4-amino-N-ethylphthalimide, which is recrystallized from methanol-water mixture. It melts at 169°–171° C.

EXAMPLE 5

3-Nitrophthalimide (30.0 g.) is ethylated with iodoethane in the same manner as the 4-nitro isomer (Example 3) to yield 35.4 g. of N-ethyl-3-nitrophthalimide melting at 102°–103° C.

EXAMPLE 6

N-Ethyl-3-nitrophthalimide (35.4 g.) is hydrogenated as in Example 4 to yield 22.5 g. of 3-amino-N-ethylphthalimide which melts at 134°–136° C.

EXAMPLE 7

A mixture of 4-amino-N-ethylphthalimide (19 g.), sodium acetate (20 g.) and acetic acid (200 ml.) are stirred together at room temperature. Bromine (20 ml.) in acetic acid (50 ml.) is added dropwise with good stirring. A heavy precipitate forms after about one-half of the bromine has been added. Stirring is continued for 3 hours after the complete addition of the bromine. The reaction mixture is drowned into water (1 l.). The product, 4-amino-3,5-dibromo-N-ethylphthalimide, is collected by filtration, washed with water and recrystallized from ethanol. It weighs 32.5 g. and melts at 186°–187° C.

EXAMPLE 8

3-Amino-N-ethylphthalimide (9.5 g.) is dibrominated using the conditions of Example 7 to yield 16 g. of 3-amino-4,6-dibromophthalimide which melts at 177°–179° C.

EXAMPLE 9

To 150 ml. of conc. $H_2SO_4$ is added portionwise with stirring at about 10° C., 3-acetamidophthalimide (41 g.). With good stirring, fuming nitric acid (30 ml.) is added gradually at 10°–15° C. The reaction mixture is stirred for 30 min. and drowned onto about 1 l. of ice-water mixture. The slightly gummy solid is collected by filtration, washed with a minimum of water and slurried in hot ethanol. The mixture is chilled and the product, 3-acetamido-6-nitrophthalimide, collected by filtration. It melts at 150°–153° C.

EXAMPLES 10–13

Sodium nitrite (2.88 g.) is added gradually to 20 ml. of conc. H₂SO₄ with stirring. The solution is cooled and 1:5 acid (40 ml.) is added below 15° C. To this mixture is added 4-amino-N-ethylphthalimide (3.8 g., 0.02 mole), followed by 40 ml. of 1:5 acid, all below 5° C. The reaction mixture is stirred at 0°–5° C. for 2 hr. The following couplers (0.005 mole) are dissolved in 25 ml. of 1:5 acid:

N-(2-Hydroxyethyl)-2,2,4,7-tetramethyl-1,2,3,4-tetrahydroquinoline (Example 10)

N-(2-Carbamoylethyl)-2,2,4,7-tetramethyl-1,2,3,4-tetrahydroquinoline (Example 11)

N-(3-Acetamidopropyl)-2,2,4,7-tetramethyl-1,2,3,4-tetrahydroquinoline (Example 12)

N-Ethyl-7-acetamido-2,2,4-trimethyl-1,2,3,4-tetrahydroqunoline (Example 13).

To each chilled coupler solution is added a 0.005 mole aliquot of diazonium salt solution. The coupling mixtures are buffered by the addition of ammonium acetate and allowed to stand for 1 hr. The azo compounds are precipitated by the addition of water, collected by filtration, washed with water, and dried in air. If needed, the azo compounds are purified by slurrying in hot methanol, cooling, filtering, and wasing with methanol.

EXAMPLES 14–15

4-Amino-5-bromo-N-ethylphthalimide (2.69 g., 0.01 mole) is diazotized using nitrosyl sulfuric acid in 1:5 acid as illustrated in Example 10. This diazonium solution is added to a chilled solution of 0.5 mole of N-(2-hydroxyethyl)-2,2,4,7-tetramethyl-1,2,3,4tetrahydroquinoline (Example 14) and 0.5 mole of N-(3-N-ethylcarbamylaminopropyl)-2,2,5,7-tetramethyl-1,2,3,4-tetrahydroquinoline (Example 15), each coupler dissolved in 25 ml. of 15% H₂SO₄. After buffering by addition of ammonium acetate, the coupling mixtures are allowed to stand 1 hr. The azo compounds are precipitated by drowning into water and are collected by filtration, washed with water and dried in air. These compounds produce deep bluish-red shades on nylon carpet and have good fastness properties.

EXAMPLE 16

4-Amino-3,5-dibromo-N-ethylphthalimide (3.48 g., 0.01 mole) is diazotized and coupled with 7-acetamido-N-ethyl-2,2,4-trimethyl-1,2,3,4-tetrahydroquinoline (2.6 g.) in 40 ml. of 1:5 acid as illustrated in Examples 10–13.

EXAMPLE 17

A mixture of 0.4 g. of the azo compound of Example 16, 0.4 g. cuprous cyanide and 20 ml. of N,N-dimethylformamide is heated at 95°–100° C. for 45 min. The reaction mixture is drowned into water. The product is collected by filtration, washed with water and dried in air. The blue dye (λmax. = 613 nm. in acetone) produces bright blue shades on polyester fibers and has the structure:

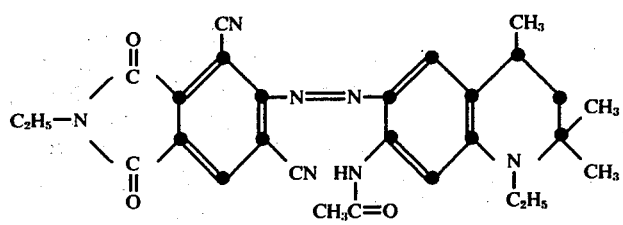

EXAMPLE 18

A mixture of 0.4 g. of the dibromo azo compound of Example 16, 3-mercapto-1(H)-1,2,4-triazole (0.4 g.), potassium carbonate (0.4 g.) N,N-dimethylformamide (20 ml.) and a trace of cuprous bromide is heated at 140°–145° C. for 30 min. and then drowned into water. The product is collected by filtration, washed with water and dried in air. It is reslurried in hot methanol, cooled, filtered and washed with methanol. This azo compound has a visible absorption maximum at 536 nm. (acetone) and produces violet shades on nylon fabrics.

The azo compounds set forth in the following table are prepared according to the synthesis techniques described herein and conform to the formula

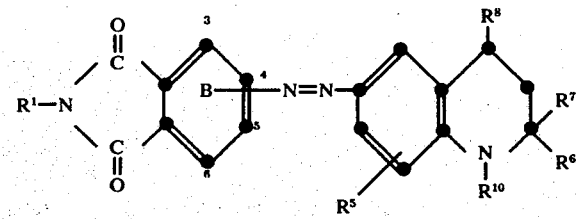

The structure of each of the azo compounds prepared in Examples 10 through 18 is set forth in the corresponding examples of the table. The phthalimidyl group is bonded to the azo group at the 4-position in the compounds of Examples 10 to 75 and at the 3-position in the compounds of Examples 76 to 132.

| Example No. | R¹ | Substituents on Ring B | R⁵, R⁶, R⁷, R⁸ | R¹⁰ | Shade Produced on Polyester Fiber |
|---|---|---|---|---|---|
| 10 | R¹ | None | 2,2,4,7-tetra-CH₃ | —CH₂CH₂OH | Red |
| 11 | —C₂H₅ | None | 2,2,4,7-tetra-CH₃ | —CH₂CH₂CONH₂ | Red |
| 12 | —C₂H₅ | None | 2,2,4,7-tetra-CH₃ | —(CH₂)₃NHCOCH₃ | Red |
| 13 | —C₂H₅ | None | 2,2,4-tri-CH₃-7-NHCOCH₃ | —C₂H₅ | Red |
| 14 | —C₂H₅ | 5-Br | 2,2,4,7-tetra-CH₃ | —CH₂CH₂OH | Bluish-red |
| 15 | —C₂H₅ | 5-Br | 2,2,4,7-tetra-CH₃ | —(CH₂)₃NHCONHC₂H₅ | Bluish-red |
| 16 | —C₂H₅ | 3,5-di-Br | 2,2,4-tri-CH₃-7-NHCOCH₃ | —C₂H₅ | Bluish-red |
| 17 | —C₂H₅ | 3,5-di-CN | 2,2,4-tri-CH₃-7-NHCOCH₃ | —C₂H₅ | Blue |
| 18 | —C₂H₅ | 3,5-di-SC=NNHCH=N | 2,2,4-tri-CH₃-7-NHCOCH₃ | —C₂H₅ | Violet |
| 19 | —C₂H₅ | None | 2,2,4,7-tetra-CH₃ | —CH₂CH₂Cl | Red |
| 20 | —CH₂CH₂OCH₃ | None | 2,2,4,7-tetra-CH₃ | —(CH₂)₃NHCOCH₃ | Red |

-continued

| Example No. | R¹ | Substituents on Ring B | R⁵, R⁶, R⁷, R⁸ | R¹⁰ | Shade Produced on Polyester Fiber |
|---|---|---|---|---|---|
| 21 | —CH₂CH₂OCH₃ | None | 2,2,4,7-tetra-CH₃ | —CH₂CH₂CONH₂ | Red |
| 22 | —C₂H₅ | None | 2,2,4,7-tetra-CH₃ | —CH₂CH₂SC=NNHCH=N (cyclic) | Red |
| 23 | —C₂H₅ | None | 2,2,4,7-tetra-CH₃ | —C₂H₅ | Red |
| 24 | —C₂H₅ | None | 2,2,4,7-tetra-CH₃ | —CH₂CH₂CN | Red |
| 25 | —CH₂CH₂OH | None | 2,2,4,7-tetra-CH₃ | —C₂H₅ | Red |
| 26 | —CH₂CH₂N(CH₂)₃CO (cyclic) | None | 2,7-di-CH₃ | —CH₂CH₂CONH₂ | Red |
| 27 | —CH₂CH₂CONH₂ | None | 2,7-di-CH₃ | —C₂H₅ | Red |
| 28 | —CH₂CH₂CH₃ | None | 2,7-di-CH₃ | —CH₂CH₂NHCOCH₃ | Red |
| 29 | —C₆H₁₁ | None | 2,2,4,7-tetra-CH₃ | —CH₂CH₂OH | Red |
| 30 | —CH₂C₆H₅ | None | 2,2,4,7-tetra-CH₃ | —CH₂CH(OH)CH₃ | Red |
| 31 | —(CH₂)₃CH₃ | None | 2,2,4-tri-CH₃ | —CH₂CH₂CONH₂ | Scarlet |
| 32 | —(CH₂)₃CH₃ | None | 2,2,4-tri-CH₃-7-Cl | —C₂H₅ | Scarlet |
| 33 | —(CH₂)₃CH₃ | None | 2,2,4-tri-CH₃-5,8-di-OCH₃ | —CH₂CH₂OH | Red |
| 34 | —(CH₂)₃CH₃ | None | 2,2,4-tri-CH₃-5,8-di-CH₃ | —CH₂CH₂CN | Scarlet |
| 35 | —(CH₂)₃CH₃ | None | 2,2,4,7-tetra-CH₃ | —CH₂CH₂OOCCH₃ | Red |
| 36 | —(CH₂)₃CH₃ | None | 2,2,4-tri-CH₃-7-NHCOCH₃ | —CH₂CH₂OOCCH₃ | Red |
| 37 | —(CH₂)₃CH₃ | None | 2,2,4-tri-CH₃-7-NHCOCH₃ | —C₂H₅ | Red |
| 38 | —(CH₂)₃CH₃ | None | 2,2,4-tri-CH₃-7-NHCOOC₂H₅ | —CH₂C₆H₅ | Red |
| 39 | —(CH₂)₃CH₃ | None | 2,2,4-tri-CH₃-7-NHCOCH₂OH | —C₂H₅ | Red |
| 40 | —(CH₂)₃CH₃ | None | 2,2,4-tri-CH₃-7-NHCOCH₂Cl | —C₂H₅ | Red |
| 41 | —C₂H₅ | 5-CH₃ | 2,2,4,7-tetra-CH₃ | —CH₂CH₂OH | Red |
| 42 | —C₂H₅ | 5-Br | 2,2,4,7-tetra-CH₃ | —CH₂CH₂CONH₂ | Red |
| 43 | —C₂H₅ | 5-Cl | 2,2,4,7-tetra-CH₃ | —CH₂CH₂OH | Red |
| 44 | —C₂H₅ | 3,5-di-Br | 2-CH₃-7-NHCOCH₃ | —C₂H₅ | Red |
| 45 | —C₂H₅ | 3,5-di-Br | 2,2,4,7-tetra-CH₃ | —CH₂CH₂OOCCH₃ | Red-brown |
| 46 | —C₂H₅ | 5-Br | 2,2,4,7-tetra-CH₃ | —C₂H₅ | Rubine |
| 47 | —C₂H₅ | 5-Br | 2,2,4,7-tetra-CH₃ | —(CH₂)₃NHCOOC₂H₅ | Rubine |
| 48 | —C₂H₅ | 5-Br | 2,2,4-tri-CH₃ | —(CH₂)₃CH₃ | Red |
| 49 | —C₂H₅ | 5-Br | 2,2,4,7-tetra-CH₃ | —(CH₂)₃NHCONHC₂H₅ | Rubine |
| 50 | —C₂H₅ | 5-Br | 2,2,4,7-tetra-CH₃ | —CH₂CH₂N(CH₂CH₂OH)-SO₂CH₃ | Red |
| 51 | —C₂H₅ | 5-Br | 2,2,4-tri-CH₃-7-NHCOC₂H₅ | —C₂H₅ | Rubine |
| 52 | —C₂H₅ | 5-CN | 2,2,4-tri-CH₃-7-NHCOC₂H₅ | —CH₂CH₂OOCCH₃ | Violet |
| 53 | —C₂H₅ | 5-CN | 2,2,4-tri-CH₃-7-NHCOC₆H₅ | —C₂H₅ | Violet |
| 54 | —C₂H₅ | 5-CN | 2,2,4,7-tetra-CH₃ | —CH₂CH₂CONH₂ | Violet |
| 55 | —C₂H₅ | 3,5-di-CN | 2-CH(CH₃)₂-7-NHCOCH₃ | —C₂H₅ | Blue |
| 56 | —C₂H₅ | 3,5-di-CN | 2-CH₃-7-NHCOCH₃ | —CH₂CH₂OOCCH₂CH(CH₃)₂ | Blue |
| 57 | —C₂H₅ | 3,5-di-CN | 2,2,4-tri-CH₃-7-NHCOCH₃ | —CH₂CH₂OOCOC₂H₅ | Blue |
| 58 | —C₂H₅ | 3,5-di-CN | 2,2,4-tri-CH₃-7-NHCOCH₃ | —CH₂CH₂C₆H₅ | Blue |
| 59 | —CH₂CH₂OOCCH₃ | 3,5-di-CN | 2,2,4-tri-CH₃-7-NHCOCH₃ | —C₂H₅ | Blue |
| 60 | —CH₂C₆H₅ | 3,5-di-CN | 2,2,4-tri-CH₃-7-NHCOCH₃ | —C₂H₅ | Blue |
| 61 | —CH₂CH₂NHCOCH₃ | 3,5-di-CN | 2,2,4-tri-CH₃-7-NHCOCH₃ | —C₂H₅ | Blue |
| 62 | —(CH₂)₃OCH₃ | 3,5-di-CN | 2,2,4-tri-CH₃-7-NHCOCH₃ | —CH₂CH₂OOCC₆H₅ | Blue |
| 63 | —C₂H₅ | 5-NO₂ | 2,2,4-tri-CH₃-7-NHCOCH₃ | —C₂H₅ | Violet |
| 64 | —C₂H₅ | 3,5-di-NO₂ | 2,2,4-tri-CH₃-7-NHCOCH₃ | —CH₂CH₂OOCCH₃ | Blue |
| 65 | —C₂H₅ | 5-SO₂C₆H₅ | 2,2,4-tri-CH₃-7-NHCOCH₃ | —CH₂CH₂OOCCH₃ | Violet |
| 66 | —C₂H₅ | 3,5-di-SO₂C₆H₅ | 2,2,4-tri-CH₃-7-NHCOCH₃ | —CH₂CH₂OOCCH₃ | Blue |
| 67 | —C₂H₅ | 5-OC₆H₅ | 2,2,4-tri-CH₃-7-NHCOCH₃ | —CH₂CH₂OOCCH₃ | Red |
| 68 | —C₂H₅ | 5-SC₆H₅ | 2,2,4-tri-CH₃-7-NHCOCH₃ | —CH₂CH₂OOCCH₃ | Rubine |
| 69 | —C₂H₅ | 5-SCH₂CH₂OH | 2,2,4-tri-CH₃-7-NHCOCH₃ | —CH₂CH₂OOCCH₃ | Rubine |
| 70 | —C₂H₅ | 5-SC=NNHCH=N (cyclic) | 2,2,4-tri-CH₃-7-NHCOCH₃ | —CH₂CH₂OOCCH₃ | Red |
| 71 | —C₂H₅ | 5-OCH₃ | 2,2,4-tri-CH₃-7-NHCOCH₃ | —CH₂CH₂OOCCH₃ | Red |
| 72 | —C₂H₅ | 3-Br-5-CH₃ | 2,2,4-tri-CH₃-7-NHCOCH₃ | —CH₂CH₂OOCCH₃ | Red |
| 73 | —C₂H₅ | 3-CN-5-CH₃ | 2,2,4-tri-CH₃-7-NHCOCH₃ | —CH₂CH₂OOCCH₃ | Violet |
| 74 | —C₂H₅ | 3-CN | 2,2,4-tri-CH₃-7-NHCOCH₃ | —CH₂CH₂OOCCH₃ | Violet |
| 75 | —C₂H₅ | 3-SO₂CH₃ | 2,2,4-tri-CH₃-7-NHCOCH₃ | —CH₂CH₂NCOCH₂CH₂CO (cyclic) | Violet |
| 76 | —C₂H₅ | 3-SO₂CH₃ | 2,2,4,7-tetra-CH₃ | —C₂H₅ | Red |
| 77 | —C₂H₅ | 3-SO₂CH₃ | 2,2,4,7-tetra-CH₃ | —CH₂CH₂CONH₂ | Scarlet |
| 78 | —C₂H₅ | 3-SO₂CH₃ | 2,2,4,7-tetra-CH₃ | —CH₂CH₂CN | Scarlet |
| 79 | —C₂H₅ | 3-SO₂CH₃ | 2,2,4,7-tetra-CH₃ | —CH₂CH₂NCOCH₂CH₂CO (cyclic) | Scarlet |
| 80 | —C₂H₅ | 3-SO₂CH₃ | 2,2,4,7-tetra-CH₃ | —(CH₂)₃NHCOCH₃ | Scarlet |
| 81 | —C₂H₅ | 3-SO₂CH₃ | 2,2,4,7-tetra-CH₃ | —CH₂CH₂OH | Scarlet |
| 82 | —C₂H₅ | 3-SO₂CH₃ | 2,7-di-CH₃ | —CH₂CH₂CONH₂ | Scarlet |
| 83 | —C₂H₅ | 3-SO₂CH₃ | 2,7-di-CH₃ | —CH₂CH₂NHCOCH₃ | Scarlet |
| 84 | —C₂H₅ | 3-SO₂CH₃ | 2,2,4,7-tetra-CH₃ | —CH₂CH₂OOCCH₃ | Scarlet |
| 85 | —C₂H₅ | 3-SO₂CH₃ | 2,2,4-tri-CH₃-7-NHCOCH₃ | —CH₂CH₂OOCCH₃ | Red |
| 86 | —C₂H₅ | 3-SO₂CH₃ | 2,2,4-tri-CH₃-7-NHCOCH₃ | —C₂H₅ | Red |
| 87 | —C₂H₅ | 3-SO₂CH₃ | 2,2,4-tri-CH₃-7-NHCOCH₃ | —CH₂CH₂CN | Red |
| 88 | —C₂H₅ | 3-SO₂CH₃ | 2,2,4-tri-CH₃-7-NHCOCH₃ | —CH₂C₆H₅ | Red |
| 89 | —C₂H₅ | 3-SO₂CH₃ | 2,2,4-tri-CH₃-7-NHCOCH₃ | —CH₂C₆H₁₁ | Red |
| 90 | —C₂H₅ | 3-SO₂CH₃ | 2,2,4-tri-CH₃-7-NHCOCH₃ | —CH₂CH₂C₆H₅ | Red |
| 91 | —C₂H₅ | 3-SO₂CH₃ | 2,2,4-tri-CH₃-7-NHCOCH₃ | —CH₂CH(OH)CH₃ | Red |
| 92 | —C₂H₅ | 3-SO₂CH₃ | 2,2,4-tri-CH₃-7-NHCOCH₃ | —CH₂CH₂N(CH₃)SO₂CH₃ | Red |
| 93 | —C₂H₅ | 3-SO₂CH₃ | 2,2,4-tri-CH₃-7-NHCOCH₃ | —CH₂CH₂OC₂H₅ | Red |
| 94 | —C₂H₅ | 3-SO₂CH₃ | 2,2,4-tri-CH₃-7-NHCOCH₃ | —(CH₂)₃NHCONHC₂H₅ | Red |
| 95 | —C₂H₅ | 3-SO₂CH₃ | 2,2,4-tri-CH₃-5,8-di-OCH₃ | —CH₂CH₂OH | Red |
| 96 | —C₂H₅ | 3-SO₂CH₃ | 2,2,4-tri-CH₃-5,8-di-CH₃ | —C₂H₅ | Red |
| 97 | —C₂H₅ | 3-SO₂CH₃ | 2,2,4-tri-CH₃-5-OCH₃-8-CH₃ | —C₂H₅ | Red |

-continued

| Example No. | R$^1$ | Substituents on Ring B | R$^5$, R$^6$, R$^7$, R$^8$ | R$^{10}$ | Shade Produced on Polyester Fiber |
|---|---|---|---|---|---|
| 98 | —CH$_2$CH$_2$CONH$_2$ | 3-SO$_2$CH$_3$ | 2,2,4-tri-CH$_3$-7-NHCOCH$_3$ | —C$_2$H$_5$ | Red |
| 99 | —(CH$_2$)$_3$OCH$_3$ | 3-SO$_2$CH$_3$ | 2,2,4-tri-CH$_3$-7-NHCOCH$_3$ | —C$_2$H$_5$ | Red |
| 100 | —C$_6$H$_{11}$ | 3-SO$_2$CH$_3$ | 2,2,4-tri-CH$_3$-7-NHCOCH$_3$ | —CH$_2$CH$_2$OOCCH$_3$ | Red |
| 101 | —CH$_2$C$_6$H$_5$ | 3-SO$_2$CH$_3$ | 2,2,4-tri-CH$_3$-7-NHCOCH$_3$ | —CH$_2$CH$_2$OOCOC$_2$H$_5$ | Red |
| 102 | —C$_2$H$_5$ | 3-SO$_2$CH$_3$ | 2,2,4-tri-CH$_3$-7-NHCOCH$_3$ | —CH$_2$CH$_2$OOCC$_2$H$_5$ | Red |
| 103 | —CH$_2$CH$_2$OH | 3-SO$_2$CH$_3$ | 2,2,4-tri-CH$_3$-7-NHCOCH$_3$ | —CH$_2$CH$_2$OOCCH$_3$ | Red |
| 104 | —CH$_2$CH$_2$NHCOCH$_3$ | 3-SO$_2$CH$_3$ | 2,2,4-tri-CH$_3$-7-NHCOCH$_3$ | —CH$_2$CH$_2$OOCCH$_3$ | Red |
| 105 | —CH$_2$CH$_2$OOCCH$_3$ | 3-SO$_2$CH$_3$ | 2,2,4-tri-CH$_3$-7-NHCOCH$_3$ | —CH$_2$CH$_2$OOCCH$_3$ | Red |
| 106 | —C$_2$H$_5$ | 4,6-di-Br | 2,2,4-tri-CH$_3$-7-NHCOCH$_3$ | —C$_2$H$_5$ | Rubine |
| 107 | —C$_2$H$_5$ | 4,6-di-Br | 2,2,4-tri-CH$_3$-7-NHCOCH$_3$ | —CH$_2$CH$_2$OOCCH$_3$ | Rubine |
| 108 | —C$_2$H$_5$ | 4-CN-6-Br | 2,2,4-tri-CH$_3$-7-NHCOCH$_3$ | —CH$_2$CH$_2$OOCCH$_3$ | Violet |
| 109 | —C$_2$H$_5$ | 4-CN-6-Br | 2,2,4-tri-CH$_3$-7-NHCOCH$_3$ | —C$_2$H$_5$ | Violet |
| 110 | —C$_2$H$_5$ | 4-NO$_2$-6-Br | 2,2,4-tri-CH$_3$-7-NHCOCH$_3$ | —C$_2$H$_5$ | Violet |
| 111 | —C$_2$H$_5$ | 4-SO$_2$C$_6$H$_5$-6-Br | 2,2,4-tri-CH$_3$-7-NHCOCH$_3$ | —C$_2$H$_5$ | Violet |
| 112 | —C$_2$H$_5$ | 4-SC$_6$H$_5$-6-Br | 2,2,4-tri-CH$_3$-7-NHCOCH$_3$ | —C$_2$H$_5$ | Rubine |
| 113 | —C$_2$H$_5$ | 4-OC$_6$H$_5$-6-Br | 2,2,4-tri-CH$_3$-7-NHCOCH$_3$ | —C$_2$H$_5$ | Rubine |
| 114 | —C$_2$H$_5$ | 4-SCH$_2$CH$_2$OH-6-Br | 2,2,4-tri-CH$_3$-7-NHCOCH$_3$ | —C$_2$H$_5$ | Rubine |
| 115 | —C$_2$H$_5$ | 6-NO$_2$ | 2,2,4-tri-CH$_3$-7-NHCOCH$_3$ | —C$_2$H$_5$ | Violet |
| 116 | —C$_2$H$_5$ | 6-NO$_2$ | 2,2,4-tri-CH$_3$-7-NHCOC$_6$H$_5$ | —C$_2$H$_5$ | Violet |
| 117 | —C$_2$H$_5$ | 6-NO$_2$ | 2,2,4-tri-CH$_3$-7-NHCOOC$_2$H$_5$ | —C$_2$H$_5$ | Violet |
| 118 | —C$_2$H$_5$ | 6-NO$_2$ | 2,2,4-tri-CH$_3$-7-NHCOC$_6$H$_5$ | —C$_2$H$_5$ | Violet |
| 119 | —C$_2$H$_5$ | 6-NO$_2$ | 2,2,4-tri-CH$_3$-7-NHCOCH$_2$OC$_6$H$_5$ | —C$_2$H$_5$ | Violet |
| 120 | —C$_2$H$_5$ | 6-NO$_2$ | 2-CH(CH$_3$)$_2$-7-NHCOCH$_2$C$_6$H$_5$ | —C$_2$H$_5$ | Violet |
| 121 | —C$_2$H$_5$ | 6-NO$_2$ | 2-CH(CH$_3$)$_2$-7-NHCOCH$_2$OH | —C$_2$H$_5$ | Violet |
| 122 | —C$_2$H$_5$ | 6-NO$_2$ | 2-CH(CH$_3$)$_2$-7-NHCOCH$_2$OOCCH$_3$ | —C$_2$H$_5$ | Violet |
| 123 | —C$_2$H$_5$ | 6-NO$_2$ | 2-CH(CH$_3$)$_2$-7-NHCOCH$_2$Cl | —C$_2$H$_5$ | Violet |
| 124 | —C$_2$H$_5$ | 4-Br-6-NO$_2$ | 2,2,4-tri-CH$_3$-7-NHCOCH$_3$ | —C$_2$H$_5$ | Violet |
| 125 | —C$_2$H$_5$ | 4-CN-6-NO$_2$ | 2,2,4-tri-CH$_3$-7-NHCOCH$_3$ | —C$_2$H$_5$ | Reddish-blue |
| 126 | —C$_2$H$_5$ | 4-SO$_2$C$_6$H$_5$-6-NO$_2$ | 2,2,4-tri-CH$_3$-7-NHCOCH$_3$ | —C$_2$H$_5$ | Reddish-blue |
| 127 | —C$_2$H$_5$ | 4,6-di-NO$_2$ | 2,2,4-tri-CH$_3$-7-NHCOCH$_3$ | —C$_2$H$_5$ | Reddish-blue |
| 128 | —C$_2$H$_5$ | 4-SO$_2$C$_2$H$_5$-6-NO$_2$ | 2,2,4-tri-CH$_3$-7-NHCOCH$_3$ | —C$_2$H$_5$ | Reddish-blue |
| 129 | —C$_2$H$_5$ | 4-OC$_6$H$_5$-6-NO$_2$ | 2,2,4-tri-CH$_3$-7-NHCOCH$_3$ | —C$_2$H$_5$ | Rubine |
| 130 | —C$_2$H$_5$ | 4-SC$_6$H$_5$-6-NO$_2$ | 2,2,4-tri-CH$_3$-7-NHCOCH$_3$ | —C$_2$H$_5$ | Violet |
| 131 | H | None | 2,2,4-tri-CH$_3$-7-NHCOCH$_3$ | —C$_2$H$_5$ | Red |
| 132 | H | 6-NO$_2$ | 2,2,4-tri-CH$_3$-7-NHCOCH$_3$ | —C$_2$H$_5$ | Violet |

The compounds of the invention can be applied to polyester by known disperse dyeing techniques employing carriers, surfactants, dispersing agents, etc. Dyeing can be conducted at atmospheric or superatmospheric pressures. The following example illustrates a dyeing procedure for applying the azo compounds of the invention to dye polyester textile materials at atmospheric pressure and at the boil:

EXAMPLE 133

The azo compound of Example 10 (0.1 g.) is dissolved in 10 cc. of 2-methoxyethanol. A small amount (3 to 5 cc.) of a 3% sodium lignin sulfonate aqueous solution is added, with stirring, and then the volume of the bath is brought to 300 cc. with water. 3 cc. of a chlorinated benzene emulsion carrier (Tanavol) is added to the bath and 10.0 g. of a textile fabric made of poly(ethylene terephthalate) fibers is placed in the bath and worked 10 min. without heat. The dyeing is carried out at the boil for 1 hr. The dyed fabric is removed from the dyebath and scoured for 20 min. at 80° C. in a solution containing 1 g./l. neutral soap and 1 g./l. sodium carbonate. The fabric is then rinsed, dried in an oven at 250° F. and heat set (for the removal of residual carrier) for 5 min. at 350° F. The fabric is dyed a bright shade of red and exhibits excellent fastness properties when tested according to conventional methods such as those described in the *Technical Manual of the American Association of Textile Chemists and Colorists*, 1968 edition.

The following example describes a method by which our compounds can be applied to texturized polyester fibers:

EXAMPLE 134

The azo compound of Example 13 (66.7 mg.) is dissolved/dispersed in 10 cc. of 2-methoxyethanol in a Launder-Ometer container to which is then added with stirring about 0.2 g. sodium lignin sulfonate and 0.2 g. of a surfactant (Igepon T-51) from a stock solution containing both components. The volume of the bath is brought to 300 ml. with water and 0.3 g. of a butyl benzoate emulsion carrier (DAC-888) is added. A fabric (10 g.) of a texturized poly(ethylene terephthalate) fiber is wet out and placed in the bath which is then sealed and affixed to the rotating arm of a Launder-Ometer set at 120° F. After placing the container-bath in rotation the Launder-Ometer is set at 260° F. and after the heating medium reaches that temperature, dyeing with rotation is continued for 1½ hours. After allowing the container-bath to cool, the dyed fabric is removed, rinsed with water and dried. If necessary, residual carrier can be removed by heat setting as described in the peceding example.

The compounds of the invention can also be applied to polyester textile materials by the heat fixation technique described in U.S. Pat. No. 2,663,612 and in the *American Dyestuff Reporter*, 42, 1 (1953). The following procedure describes how the azo compounds of the invention can be applied to polyester materials by the heat fixation technique:

EXAMPLE 135

A mixture of 500 mg. of the compound of Example 17, 150 mg. of a sodium lignosulfonate dispering agent (Marasperse N), 150 mg. of a partially desulfonated sodium lignosulfonate (Marasperse CB), 0.5 ml. glycerin, and 1.0 ml. of water is ground in a micro-size container (an accessory for a 1-quart size Szegvari Attritor) for approximately 3.5 hrs. Enough ⅛-inch stainless steel balls are added to provide maximum grinding. When the grinding is complete, the entire contents are poured into a beaker and 100 ml. of water are used to wash the remaining dye paste from the micro-container. The dye paste is then heated slowly to 65° C. with continuous stirring. A thickener and penetrating mixture is prepared by mixing 1 ml. of a complex diaryl sulfonate surfactant (Compound 8-S),
3 ml. of a 3% solution of a sodium N-methyl-N-oleoyltaurate (Igepon T-S1),
8 ml. of a 25% solution of natural gums (Superclear 80N), and sufficient water to bring the volume to 100 ml.

The thickener and penetrating mixture is added to the dye paste, the volume is adjusted to 200 ml. and the mixture is agitated for 15 min. The dye mixture is then filtered through cheesecloth to remove the stainless steel balls and added to the reservoir of a Butterworth padder where it is heated to about 45° to 60° C. 10 g. of a fabric of poly(ethylene terephthalate) fibers and 10 g. of a fabric of 65/35 spun poly(ethylene terephthalate)/cotton fibers are sewn together, end-to-end, and padded for 5 min. of continuous cycling through the dye mixture and between three rubber squeeze rollers of the padder. Dye mixture pick-up is about 60% based on the weight of the fabrics. The padded fabrics are dried at 200° F. and then heat-fixed for 2 min. at 415° F. in a forced air oven. The dyed fabrics are scoured for 20 min. at 65° to 70° C. in a solution containing 0.2% sodium hydrosulfite, 0.2% sodium carbonate and 1.7% of a 3% solution of sodium N-methyl-N-oleoyltaurate and then dried. The dyed fabrics possess excellent brightness and fastness to light and sublimation.

The heat fixation dyeing procedure described above can be varied by the substitution of other dispersing agents, surfactants, suspending agents, thickeners, etc. The temperature and time of the heat-fixation step can also be varied.

Fibers having a basis of a linear terephthalate polyester and sold under the trademarks "Kodel", "Dacron", "Fortrel", "Vycron" and "Terylene" are illustrative of the linear aromatic polyester textile materials that can be dyed with the novel azo compounds. Polyesters prepared from ethylene glycol and dimethylterephthalate and cyclohexanedimethanol and dimethylterephthalate are examples of such linear aromatic polyesters. Polyesters prepared from cyclohexanedimethanol and dimethylterephthalate are more particularly described in U.S. Pat. No. 2,901,466. Poly(ethylene terephthalate) polyester fibers are described, for example, in U.S. Pat. No. 2,465,319. The polymeric linear polyester materials disclosed in U.S. Pat. No. 2,945,010; 2,957,745 and 2,989,363, for example, can be dyed. The linear aromatic polyester materials specifically named have a melting point of at least 0.35 and preferably, about 0.6. The inherent viscosity of the poly(1,4-cyclohexylenedimethylene terephthalate) polymer is also at least 0.35. These inherent viscosities are measured at 25° C. using 0.25 g. polymer per 100 ml. of a solvent consisting of 60% phenol and 40% tetrachloroethane. The polyester fabrics, yarns, fibers and filaments that are dyed with the novel azo compounds can also contain minor amounts of other additives such as brighteners, pigments, delusterants, inhibitors, stabilizers, etc.

The invention has been described in detail with particular reference to preferred embodiments thereof, but it will be understood that variations and modifications can be effected within the spirit and scope of the invention.

We claim:
1. A disperse dye azo compound having the formula

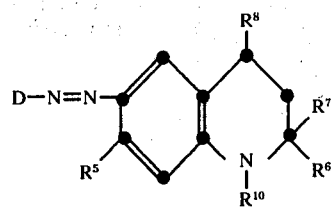

wherein group
D is a phthalimidyl goup having the formula

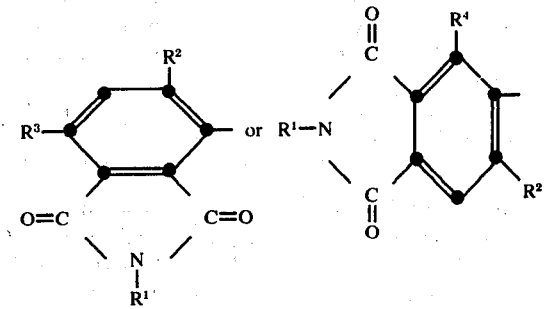

wherein $R^1$ is hydrogen, alkyl of 1–4 carbons, arylmethyl, cyclohexylmethyl, 2-cyanoethyl, 2-carbamoylethyl, aryl, cyclohexyl, or the group —Z—$R^{17}$ in which Z is ethylene, propylene, or trimethylene and $R^{17}$ is succinimido, glutarimido, phthalimido, hydroxy, alkanoyloxy of 1–4 carbons, 2-pyrrolidinone, or alkoxy of 1–4 carbons;

$R^2$ is hydrogen, alkyl of 1–4 carbons, chlorine, bromine, cyano, nitro, alkylsulfonyl of 1–4 carbons, arylsulfonyl, arylthio, arylalkylthio where the alkyl is of 1–4 carbons, cyclohexylthio, alkoxy of 1–4 carbons, aryloxy, 2-benzothiazolylthio, 2-thiazolylthio, 2-thiadiazolylthio, 2-oxadiazolylthio, 1,2,4-triazol-3-ylthio, or 2-pyrimidinylthio;

$R^3$ is hydrogen, chlorine, bromine or nitro;

$R^4$ is hydrogen, alkyl of 1–4 carbons, chlorine, bromine, cyano, nitro, alkylsulfonyl of 1–4 carbons, arylsulfonyl, arylthio, arylalkylthio where the alkyl is of 1–4 carbons, cyclohexylthio, alkoxy of 1–4 carbons, aryloxy, 2-benzothiazolylthio, 2-thiazolylthio, 2-thiadiazolylthio, 2-oxadiazolylthio, 1,2,4-triazol-3-ylthio, or 2-pyrimidinylthio;

$R^5$ is hydrogen, methyl, chlorine, acetamido, benzamido, —NHCOCH$_2$Cl, —NHCOCH$_2$OH, —NHCOOC$_2$H$_5$, —NHCOCH$_2$OC$_6$H$_5$, or —NHCOCH$_2$OOCCH$_3$;

$R^6$ is alkyl of 1–4 carbons or, when $R^7$ and $R^8$ each is methyl, $R^6$ is methyl;

$R^7$ and $R^8$ each is hydrogen or methyl;

$R^9$ is formyl, alkanoyl of 1–6 carbons, alkanoyl of 1–6 carbons substituted with chlorine, bromine, phenyl or phenyl substituted with alkyl of 1–4 carbons, chlorine, bromine, or alkoxy of 1–4 carbons, cyano, alkoxy of 1–6 carbons, phenoxy, benzyloxy, alkythio of 1–6 carbons, alkylsulfonyl of 1–6 carbons, or alkanoyloxy of 1–6 carbons;

$R^{10}$ is alkyl containing one to eight carbon atoms; cyclohexyl; cyclohexyl substituted with alkyl of 1–4 carbon atoms; or alkyl of 1–4 carbons substituted with hydroxy, lower alkoxy, aryl, aryloxy, cyclohexyl, cyano, alkanoyloxy of 1–4 carbons, alkoxycarbonyl of 1–4 carbons, alkoxycarbonyloxy of 1–4 carbons, aroyloxy, alkylcarbamoyloxy of 1–4 carbons, arylcarbamoyloxy, or a group having the formula

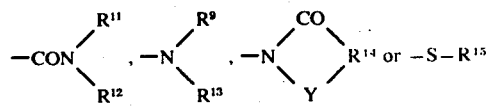

wherein
$R^{11}$ individually is hydrogen, alkyl of 1–4 carbons, phenyl or phenyl substituted with alkyl of 1–4 carbons, chlorine, bromine or alkoxy of 1–4 carbons,
$R^{12}$ individually is hydrogen or alkyl of 1–4 carbons,
$R^{11}$ and $R^{12}$ collectively are —(CH$_2$)$_5$— or —CH$_2$CH$_2$OCH$_2$CH$_2$—,
$R^{13}$ is hydrogen, alkyl of 1–4 carbons, phenyl or phenyl substituted with alkyl of 1–4 carbons, chlorine, bromine or alkoxy of 1–4 carbons, or cyclohexyl,
$R^{14}$ is ethylene, propylene, trimethylene, o-cyclohexylene, or o-arylene, or when Y is —CO—, $R^{14}$ also can be —NHCH$_2$—, —N(alkyl of 1–4 carbons)CH$_2$—, —SCH$_2$—, or —CH$_2$OCH$_2$—,
Y is —CH—, —CO—, or —SO$_2$—, and
$R^{15}$ is phenyl or phenyl substituted with alkyl of 1–4 carbons, chlorine, bromine, or alkoxy of 1–4 carbons, benzyl, cyclohexyl, 1,2,4-triazol-3-yl, or 2-benzothiazolyl,
in which each aryl moiety of $R^1$, $R^2$, $R^4$, $R^{10}$ and $R^{14}$, is phenyl or phenyl mono- or disbustituted with alkyl of 1–4 carbons, alkoxy of 1–4 carbons, chlorine or bromine.

2. A compound according to claim 1 having the formula

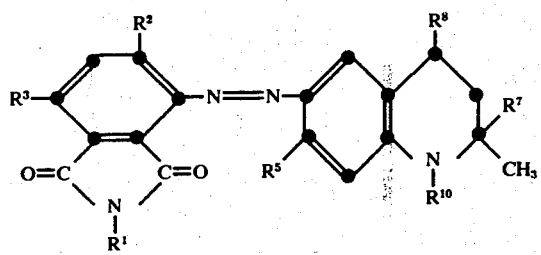

-continued
or

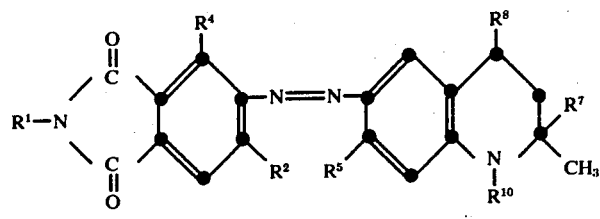

wherein
$R^1$ is hydrogen; alkyl of 1–4 carbons; arylmethyl, cyclohexylmethyl; 2-cyanoethyl; 2-carbamoylethyl; aryl; cyclohexyl; or the group —Z—$R^{17}$ in which Z is ethylene, propylene, or trimethylene and $R^{17}$ is succinimido, glutarimido, phthalimido, hydroxy, lower alkanoyloxy, 2-pyrrolidinone, or lower alkoxy;
$R^2$ is hydrogen, chlorine, bromine or cyano;
$R^3$ is hydrogen, chlorine, bromine or nitro;
$R^4$ is hydrogen, chlorine, bromine or cyano;
$R^5$ is hydrogen, methyl, chlorine, acetamido, benzamido, —NHCOCH$_2$Cl, —NHCOCH$_2$OH, —NHCOOC$_2$H$_5$, —NHCOCH$_2$OC$_6$H$_5$, —NHCOCH$_2$OOCCH$_3$;
$R^7$ and $R^8$ each is hydrogen or methyl; and
$R^{10}$ is alkyl of 1–4 carbons; cyclohexyl; arylmethyl; cyclohexylmethyl; 2-cyanoethyl; 2-carbamoylethyl; N-lower alkyl-2-carbamoylethyl wherein the alkyl moiety contains 1–4 carbons; N,N-di-lower-alkyl-2-carbamoylethyl wherein the alkyl moiety contains 1–4 carbons; or the group —Z—$R^{16}$ in which Z is ethylene, propylene or trimethylene and $R^{16}$ is hydroxy, alkanoyloxy of 1–4 carbons, alkoxycarbonyl of 1–4 carbons, alkoxycarbonyloxy of 1–4 carbons, succinimido, glutarimido, phthalimido, 2-pyrrolidinono, alkanoylamino of 1–6 carbons, lower alkoxy or the group

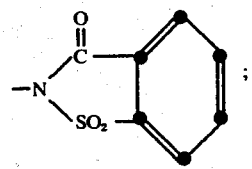

in which each aryl moiety is phenyl, tolyl, anisyl, ethoxyphenyl or chlorophenyl.

3. A compound according to claim 1 having the formula

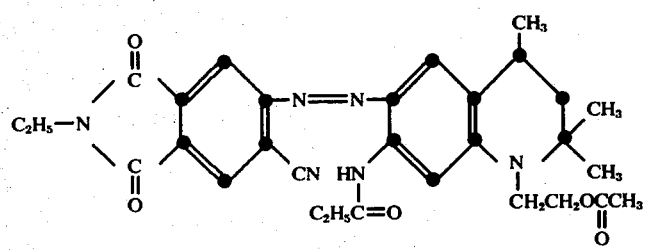

4. A compound according to claim 1 having the formula

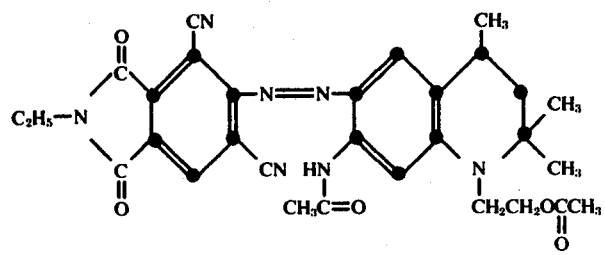
5. A compound according to claim 1 having the formula
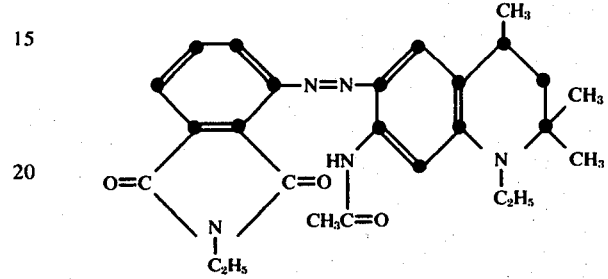
6. A compound according to claim 1 having the formula
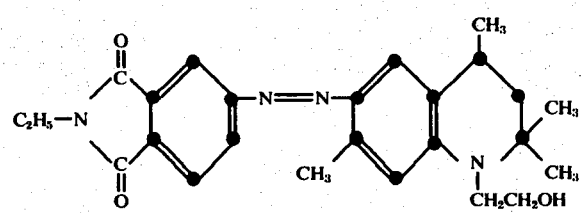
7. A compound according to claim 1 having the formula
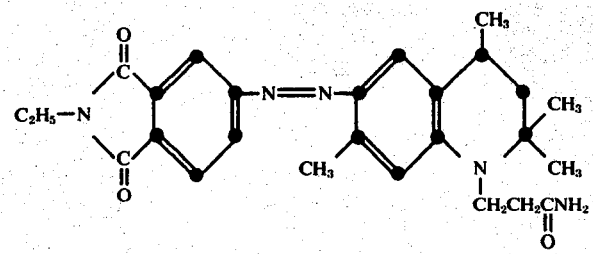
8. A compound according to claim 1 having the formula
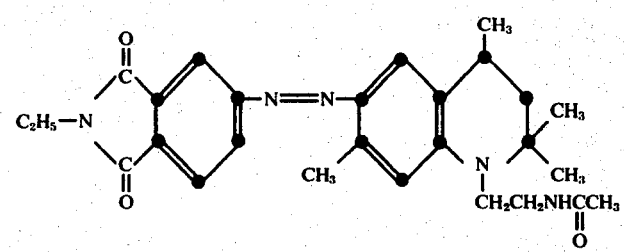
* * * * *